United States Patent [19]

Karami

[11] 4,090,515

[45] May 23, 1978

[54] DISPOSABLE DIAPER WITH WAIST FLUID BARRIER

[75] Inventor: Hamzeh Karami, Crystal Lake, Ill.

[73] Assignee: Colgate-Palmolive Company, New York, N.Y.

[21] Appl. No.: 764,611

[22] Filed: Feb. 1, 1977

Related U.S. Application Data

[63] Continuation of Ser. No. 634,578, Nov. 24, 1975, abandoned.

[51] Int. Cl.² .......................................... A61F 13/16
[52] U.S. Cl. .................................... 128/284; 128/287
[58] Field of Search .................. 128/284, 287, 290 R, 128/296

[56] References Cited

U.S. PATENT DOCUMENTS

| | | | |
|---|---|---|---|
| 3,629,039 | 12/1971 | Frick | 156/383 |
| 3,777,758 | 12/1973 | Mesek et al. | 128/284 |
| 3,794,038 | 2/1974 | Buell | 128/287 |
| 3,863,637 | 2/1975 | MacDonald | 128/287 |

Primary Examiner—John D. Yasko

Attorney, Agent, or Firm—Powell L. Sprunger

[57] ABSTRACT

A disposable diaper comprising, an absorbent pad assembly having a pair of side edges, and an absorbent pad having a pair of side edges and a pair of end edges connecting the side edges. The pad assembly has a fluid impervious backing sheet covering a back surface of the pad and having at least one end section extending past one end edge of the pad and defining an end edge of the pad assembly, with the end section extending between the side edges of the pad assembly. The pad assembly has a fluid pervious top sheet covering a front surface of the pad, and a separate segment of fluid impervious material overlying the end section of the backing sheet and extending substantially between the side edges of the pad assembly. The segment extends inwardly from the end edge of the pad assembly toward the longitudinal center of the diaper and overlies an end portion of the top sheet and pad adjacent the one end edge of the pad to prevent leakage from the end of the pad, with the segment being secured to the underlying portion of the pad assembly substantially throughout the lateral and longitudinal dimensions of the segment.

7 Claims, 4 Drawing Figures

U.S. Patent    May 23, 1978    4,090,515
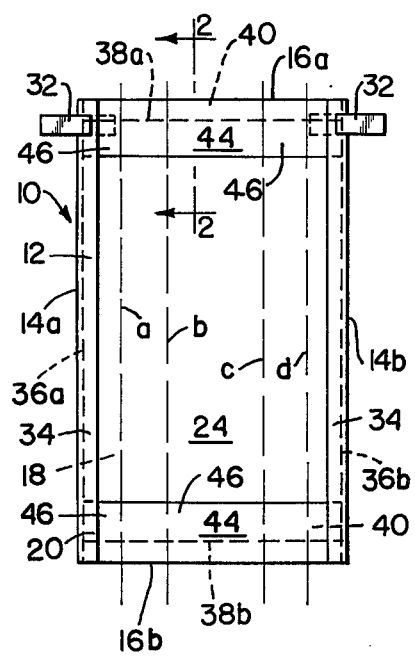
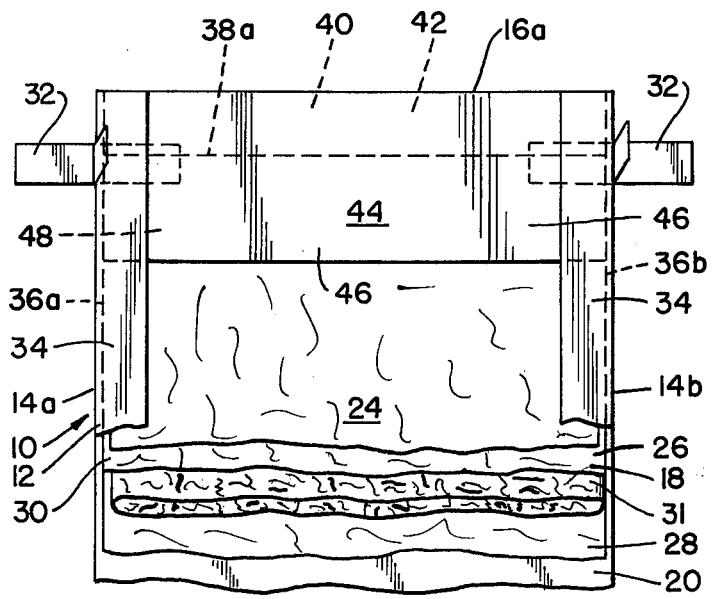
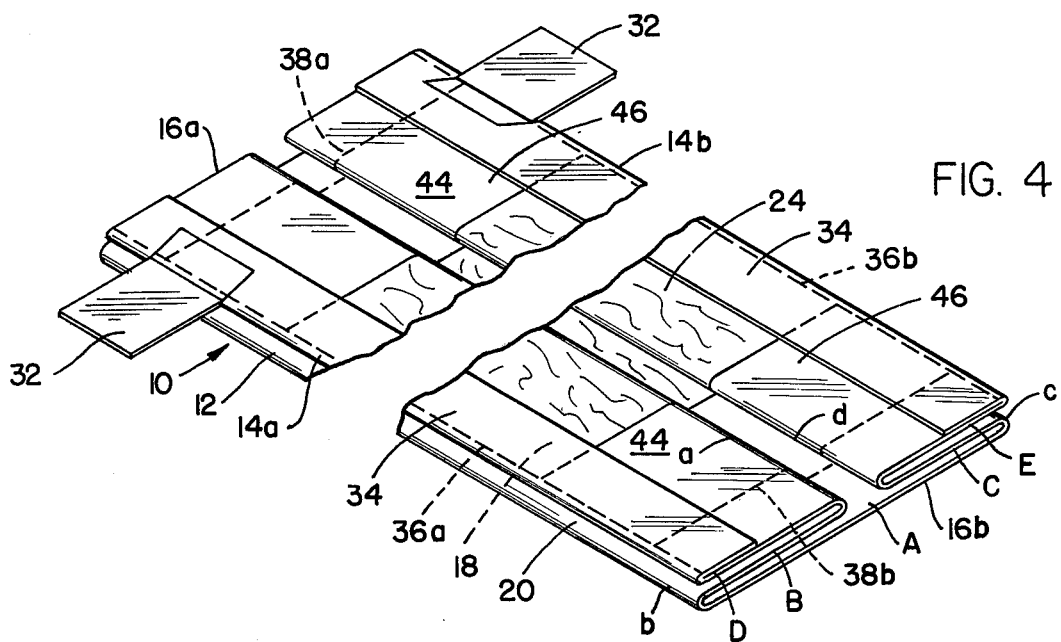
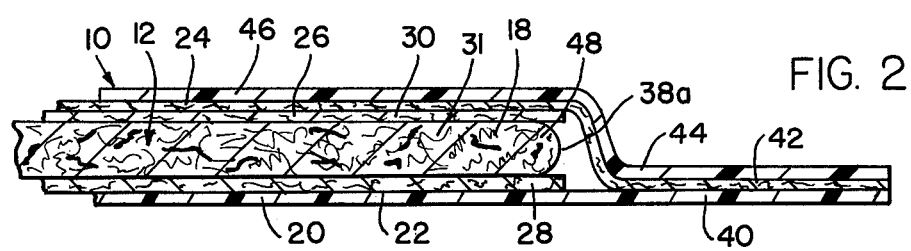

DISPOSABLE DIAPER WITH WAIST FLUID BARRIER

This is a continuation of application Ser. No. 634,578, filed Nov. 24, 1975 and now abandoned.

BACKGROUND OF THE INVENTION

The present invention relates to absorbent articles, and more particularly to disposable diapers.

In recent years, diapers of the disposable type have come into widespread use due to convenience of parents, since such diapers may be discarded after a single use. Although in many respects satisfactory for their intended purpose, a recurrent problem encountered in such diapers has been leaking or wicking of urine from end edges of the diapers. Placement of fluid barriers inside the diaper ends does not totally solve this difficulty, since a top sheet of the diaper located over such barriers wicks urine past the barriers, and causes leakage from the diaper ends. Also, it may be relatively difficult to fold an end of a backing sheet in the diaper over the top of the diaper during the manufacturing procedure depending upon the manufacturing equipment used.

SUMMARY OF THE INVENTION

A principal feature of the present invention is the provision of a disposable diaper of simplified construction to prevent leakage at ends of the diaper.

The diaper of the present invention comprises, an absorbent pad assembly having a pair of side edges, and an absorbent pad having a pair of side edges and a pair of end edges connecting the side edges. The pad assembly has a fluid impervious backing sheet covering a back surface of the pad and having at least one end section extending past one end edge of the pad and defining an end edge of the pad assembly, with the end section extending substantially between side edges of the pad assembly. The pad assembly has a fluid pervious top sheet covering a front surface of the pad, and a separate segment of fluid impervious material overlying the end section of the backing sheet and extending substantially between the side edges of the pad assembly. The segment extends inwardly from the end edge of the pad assembly toward the longitudinal center of the diaper and overlies an end portion of the top sheet and pad adjacent the one end edge of the pad. The segment is secured to the underlying portion of the pad assembly substantially throughout the lateral and longitudinal dimensions of the segment.

A feature of the present invention is that the end section of the backing sheet and the segment of fluid impervious material provides a barrier at the end of the diaper to prevent leakage of urine from the diaper.

Another feature of the present invention is that the segment of fluid impervious material covers an end portion of the top sheet and prevents the top sheet from wicking urine over the segment.

Yet another feature of the invention is that the diaper of the present invention may be made in a simplified manner during the manufacturing procedure.

Further features will become more fully apparent in the following description of the embodiments of this invention and from the appended claims.

DESCRIPTION OF THE DRAWINGS

In the drawings:

FIG. 1 is a plan view of a disposable diaper of the present invention;

FIG. 2 is a fragmentary sectional view taken substantially as indicated along the line 2—2 of FIG. 1;

FIG. 3 is a fragmentary plan view of the diaper of FIG. 1; and

FIG. 4 is a fragmentary perspective view of the diaper of FIG. 1 as folded into a box-pleat configuration.

DESCRIPTION OF THE PREFERRED EMBODIMENTS

Referring now to FIG. 1, there is shown a disposable diaper generally designated 10 having an absorbent pad assembly 12. As illustrated in FIGS. 1-3, the pad assembly 12 has a pair of side edges 14a and 14b, and a pair of end edges 16a and 16b connecting the side edges 14a and b. As best shown in FIGS. 2 and 3, the pad assembly 12 has an absorbent pad 18, a fluid impervious backing sheet 20, such as polyethylene, covering a back surface 22 of the pad 18, and a fluid pervious top sheet 24 covering a front surface 26 of the pad 18. The pad 18 may be made of a back wadding sheet 28, a front wadding sheet 30, and an absorbent filler 31, such as wood fluff, positioned between the back and front wadding sheets 28 and 30, respectively. As illustrated in FIGS. 1 and 3, the diaper 10 may have a pair of conventional tape fasteners 32 for securing the diaper about an infant during placement of the diaper. The backing sheet 20 may have lateral side margins 34 folded over and secured to the front of the pad assembly, as shown. The absorbent pad 18 itself has a pair of side edges 36a and 36b, and a pair of end edges 38a and 38b connecting the side edges 36a and b. As shown, the side edges 36a and b of the pad 18 are located adjacent the side edges 14a and b of the pad assembly 12, such that the side margins 34 of the backing sheet 20 form a fluid impervious barrier adjacent the sides of the diaper, while the end edges 38a and b of the pad 18 are spaced from the end edges 16a and b of the pad assembly 12.

As best shown in FIGS. 1 and 2, the backing sheet 20 includes a pair of end sections 40 extending past the end edges 38a and b of the pad 18 adjacent each end of the diaper and defining the end edges 16a and b of the pad assembly 12. Also, the top sheet 24 includes a pair of end sections 42 extending past the end edges 38a and b of the pad 18 at both ends of the pad assembly 12, and in a preferred form, the end sections 42 of the top sheet 24 extend to the end edges 16a and b of the pad assembly 12, as shown.

In accordance with the present invention, the pad assembly 12 has a pair of end segments 44 of a fluid impervious material, such as polyethylene, located at both ends of the pad assembly 12. As shown, the segments 44 extend substantially the width of the pad assembly 12 between the side edges 14a and b. Also, the segments 44 extend from the end edges 16a and b of the pad assembly inwardly toward the lateral central region of the pad assembly 12, with an inner portion 46 of the segments 44 overlying an end portion 48 of the pad 18, in addition to the top sheet 24 and the backing sheet sections 40. The segments 44 are preferably secured or laminated substantially throughout their lateral and longitudinal dimensions to the underlying portion of the pad assembly 12, in this case the top sheet 24. The segments 44 may be secured to the diaper by adhesive, or may be heat sealed to bond the segments to the top sheet where a thermoplastic material, such as polyethylene, is used for the segments 44.

The fluid impervious segments 44 serve as a barrier at the ends of the absorbent pad 18 to prevent urine wicking and leakage from the ends of the pad 18. Also, the segments 44 are bonded to the outer surface of the top sheet 24, such that the top sheet 24 is prevented from wicking urine over the outside of the segments 44. As best shown in FIGS. 1 and 3, the lateral side margins 34 of the backing sheet 20 may be folded over the front surface of the fluid impervious segments 44, such that the side margins 34 and segments 44 provide a fluid impervious barrier extending completely around the sides of the absorbent pad 18. In addition, the segments may be positioned over the top of the diapers during the manufacture procedure, thus eliminating the necessity for folding over ends of the backing sheet to form an end barrier and simplifying the procedure.

As illustrated in FIGS. 1 and 4, the flat diaper may be folded along a plurality of longitudinally extending fold lines *a, b, c,* and *d* to form a box-pleat configuration of the diaper, as shown in FIG. 4. The box-pleat diaper has a longitudinally extending central panel A, a pair of first panels B and C extending from and overlying the front surface of the central panel A and a pair of second panels D and E extending from and overlying the first panels B and C.

The foregoing detailed description is given for clearness of understanding only, and no unnecessary limitations should be understood therefrom, as modifications will be obvious to those skilled in the art.

I claim:

1. A disposable diaper, comprising:
   an absorbent pad assembly having a pair of side edges, an absorbent pad having a pair of side edges and a pair of end edges connecting the side edges, a fluid impervious backing sheet covering a back surface of said pad and having at least one end section extending past one end edge of the pad and defining an end edge of the pad assembly, with said end section extending between side edges of the pad assembly, said pad assembly having a fluid pervious top sheet covering a front surface of the pad, and a separate segment of fluid impervious material overlying said end section of the backing sheet and extending substantially between the side edges of the pad assembly, said segment extending inwardly from the end edge of the pad assembly toward the longitudinal center of the diaper and overlying an end portion of the top sheet and pad adjacent said one end edge of the pad to prevent fluid leakage from the end of the pad, said segment being secured to the underlying portion of the pad assembly substantially throughout the lateral and longitudinal dimensions of the segment.

2. The diaper of claim 1 wherein said top sheet extends to the end edge of the pad assembly, and in which said segment is secured to an outer surface of the top sheet substantially throughout the lateral and longitudinal dimensions of said segment.

3. The diaper of claim 1 wherein said segment is made of a thermoplastic material and is sealed to the underlying portion of the diaper.

4. The diaper of claim 1 wherein said backing sheet includes lateral side margins folded over and secured to the front of the diaper.

5. The diaper of claim 4 wherein a portion of the backing sheet side margins overlie side margins of said segment.

6. The diaper of claim 1 wherein the side edges of the pad are located adjacent the side edges of the pad assembly.

7. The diaper of claim 1 including a plurality of longitudinally extending folds defining a box-pleat configuration of the diaper.

* * * * *